United States Patent [19]

Behm et al.

[11] Patent Number: 5,006,227

[45] Date of Patent: Apr. 9, 1991

[54] VOLUMETRIC FLOW CONTROLLER FOR AEROSOL CLASSIFIER

[75] Inventors: Steven M. Behm, Minneapolis; Virgil A. Marple, Maple Plain, both of Minn.; Robert M. Burton, Raleigh, N.C.

[73] Assignee: MSP Corporation, Minneapolis, Minn.

[21] Appl. No.: 371,986

[22] Filed: Jun. 26, 1989

[51] Int. Cl.⁵ .................................................. B07B 7/00
[52] U.S. Cl. ...................................... 209/143; 73/28.01
[58] Field of Search ........................ 209/142, 143, 154; 55/21, 213, 271, 417; 73/28, 865.5; 137/118, 12, 883

[56] References Cited

U.S. PATENT DOCUMENTS

| | | | |
|---|---|---|---|
| 3,261,199 | 7/1966 | Raynor | 73/28 |
| 3,413,998 | 12/1968 | Vaughan | 137/118 |
| 3,501,899 | 3/1970 | Allen | 55/417 X |
| 3,556,126 | 1/1971 | Oswald | 137/118 |
| 3,605,485 | 9/1971 | Badzioch et al. | 73/28 |
| 3,731,464 | 5/1973 | Brumbaugh et al. | 209/143 X |
| 3,965,748 | 6/1976 | Boubel et al. | 73/28 X |
| 4,301,002 | 11/1981 | Loo | 209/143 |
| 4,473,326 | 9/1984 | Oetiker | 55/417 X |
| 4,670,135 | 6/1987 | Marple et al. | 209/143 |
| 4,767,524 | 8/1988 | Yeh et al. | 209/143 |

*Primary Examiner*—Michael S. Huppert
*Assistant Examiner*—Edward M. Wacyra
*Attorney, Agent, or Firm*—Kinney & Lange

[57] ABSTRACT

A volumetric flow controller is used in connection with a virtual impactor classifier to control two separate flows in separate lines from an air pump. Each line has a flow control valve controlled in response to flow signals that are obtained from a pressure transducer that provides an electrical signal proportional to pressure. Pressure changes are sensed and the provided electrical signal is compared with a reference and will actuate a damper motor and move a flow control butterfly valve in the flow line for adjusting the flow when the pressure signal is different from the reference. The circuitry used provides for a dead band, so that changes in the butterfly valve setting will not occur unless the flow varies a selected amount, and also a timer control is used so that the motor operating the damper will be operated only at selected time intervals to prevent "hunting" or continuous operation of the valves. Further, temperature compensation signals can be provided as desired. The ability to control the flow volume provides for more accurate aerosol sampling and cut off points for the size of particles being sampled.

12 Claims, 1 Drawing Sheet

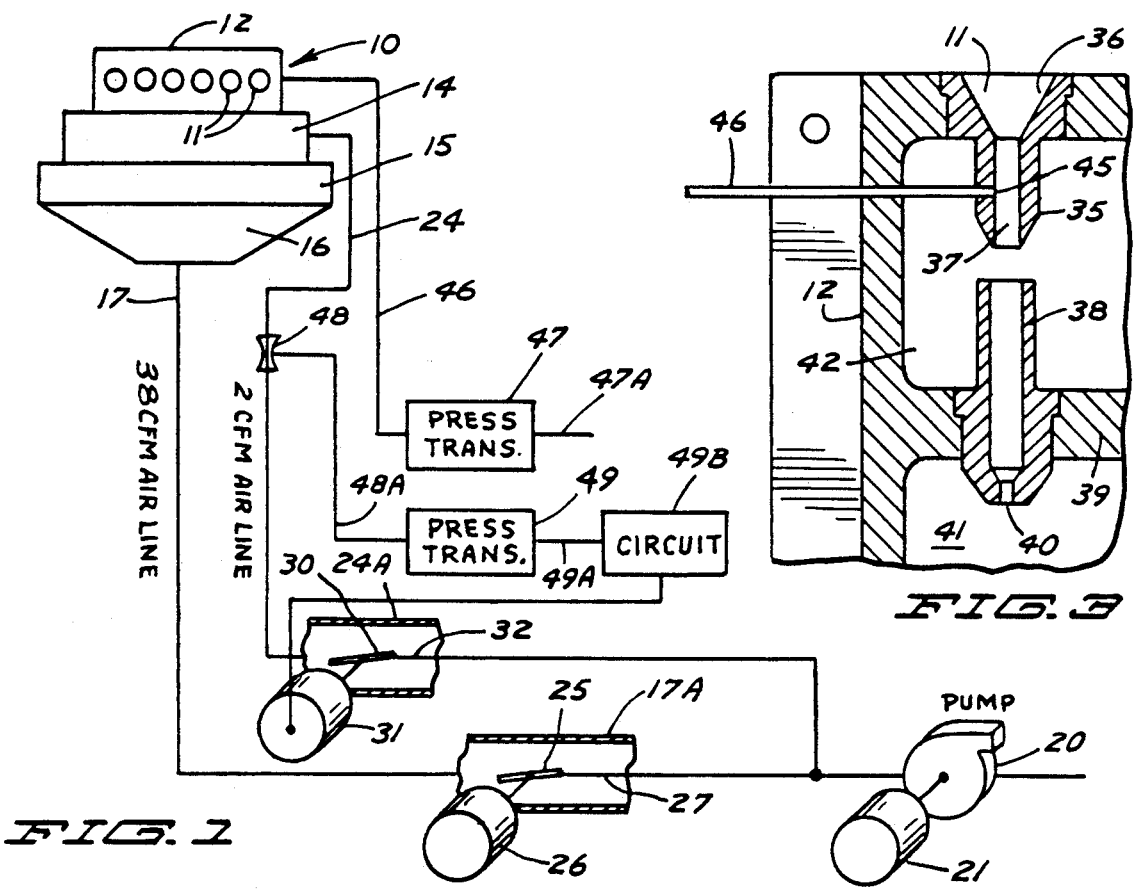
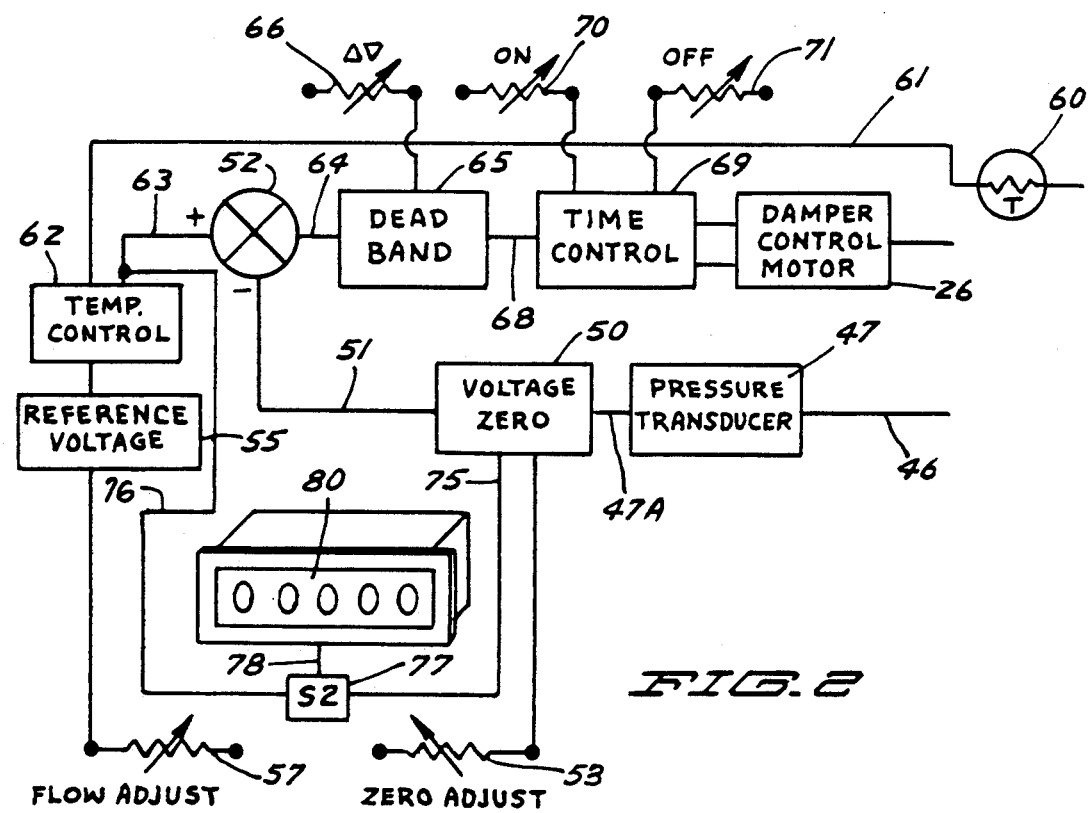

VOLUMETRIC FLOW CONTROLLER FOR AEROSOL CLASSIFIER

BACKGROUND OF THE INVENTION

1. Field of the Invention

The present invention relates to volumetric flow controls for aerosol samplers or classifiers which maintain inlet flow volume at a desired level.

2. Description of the Prior Art

Various types of aerosol classifier been advanced, and the assignee of the present application is the Licensee of U.S. Pat. No. 4,670,135, which illustrates a nozzle type high volume virtual impactor. The device shown in U.S. Pat. No. 4,670,135 is the type of device utilizing the present volumetric flow control.

Other prior art classification devices have used hot wires for sensing flow, which provides mass flow control, and sensors such as critical venturi have been used for controlling mass flow in inlets to some types of classifiers. However, the operation of the classifiers of the virtual impactor type is flow volume dependent, and the present invention provides a way of controlling volumetric flow simply, easily, and reliably.

SUMMARY OF THE INVENTION

The present invention relates to a flow volume flow control for an aerosol classifier, as shown a high volume virtual impactor classification device that has a pressure sensor in the desired flow passage, to provide a pressure signal to a transducer which in turn provides an output that is processed with respect to a reference flow signal. When a pressure change of significant magnitude occurs (greater than a dead band), a signal is passed through a timer control to operate a reversible motor which controls a damper.

Damper control provides a precise volume control for the sensed line.

In a multiple nozzle inlet, high volume virtual impactor, the sensor as shown is preferably a static pressure sensor directly in one of the inlet nozzles.

One of the advantages of using flow control valves in the flow lines is that the vacuum pump used for the classifier can be larger than the precise flows needed so that as filters tend to plug adjustments with the butterfly valves will permit the required flow to continue.

The control circuit provides for long term reliable operation in a variety of ambient conditions, and includes compensations for wide temperature variations.

BRIEF DESCRIPTION OF THE DRAWINGS

FIG. 1 is a schematic representation of a high volume aerosol sampler having a flow control system made according to the present invention;

FIG. 2 is a schematic representation of a control circuit for the device of the present invention; and FIG. 3 is an enlarged sectional view through one of the inlet nozzles of the sampler of FIG. 1 showing the static sensing port therein.

DETAILED DESCRIPTION OF THE PREFERRED EMBODIMENT

FIG. 1 is a schematic layout of the present invention, and illustrates a high volume virtual impactor 10 that includes a plurality of inlet nozzles 11, mounted on a housing 12. This device is illustrated in detail in U.S. Pat. No. 4,670,135, issued June 2, 1987. The housing 12 mounts a plurality of the nozzles that are shown in greater detail in FIG. 3, and the flows include a primary outlet flow of approximately 38 cubic feet per minute, and a low volume secondary outlet flow causing particle separation at a desired cut off size. The secondary flow is in the range of 2 cubic feet per minute so the total flow through the inlet nozzles 11 is 40 cfm. A housing section 14 is positioned below the nozzles 11. A filter assembly through which the main flow is passed or will be used for collecting particles in the air flow. The filter is carried in a housing block 15 below the housing section 14, and a tapered lower housing section 16 leads to a main output airflow conduit 17. The airflow conduit 17 is of suitable size to carry 38 cubic feet per minute. The conduit is shown in detail at 17A along with a conduit flow control valve, as which will be explained. Conduit 17 leads to the impactor from a vacuum pump 20. Pump 20 is a pump conventionally used with aerosol sampling devices and is driven by a motor 21 for providing a flow through the sampling device.

The secondary flow conduit is indicated generally at 24 and is shown in detail at 24A, and this conduit connects into the conduit leading to the pump 20. The conduit has suitable restrictors in it so that the flows are properly adjusted at desired levels. The 2 cubic feet per minute flow is bled off at housing section 14 and does not pass through the main filter held by housing 15. The pump 20 can have a higher capacity than the total flow that is needed for the classification device 10, because of the provision of precisely controlled flow volume control dampers in the conduits 17 and 24.

As shown, the conduit section 17A has a butterfly type damper valve 25 therein which is adjusted by a schematically shown reversible motor 26 that can be precisely rotated to position the damper 25 at any desired angle with respect to the longitudinal axis 27 of the conduit 17.

A flow control butterfly valve 30 is used in the 2 cubic feet per minute line 24, and is driven by a reversible motor 31 that also can be precisely controlled in rotational position in either direction of rotation. The angle of the plane of the butterfly type damper valve 30 can thus be adjusted with respect to the axis 32 of the conduit 24.

In order to control the flow volume control motors 26 and 31, pressure drops are sensed at suitable locations for accurately determining the flows, and these flow dependent signals are used as feedbacks to adjust the respective valves for changing the volume of air flowing through the classifier device 10.

FIG. 3 shows the housing 12 of the classifier in fragmentary cross section, including one of the inlet nozzles 11. As can be seen, the inlet nozzle 11 is formed in a nozzle housing 35 that has an inlet passageway 36, and a central nozzle portion 37 that is axially aligned with a receiver tube 38 that is mounted on a second wall 39 of the housing. The receiver tube 38 receives the minor flow, which flow is present in a chamber 41. A substantial number of inlet nozzles are arranged around the sides of the housing 12. The minor flow is proportioned to each nozzle and receiver tube. An orifice 40 on the inner end of each receiver tube 38 acts in part as a flow controller. The conduit 24 is connected to chamber 41 to draw air through the receiver tube 38 and into the chamber 41. The major flow passes through the chamber 42 (and a like chamber on the opposite side of the housing) to the line 17. The major flow from all of the nozzles 11 forms the 38 cubic feet per minute volume. The major flow thus flows through the space between the inner end of the nozzle housing 35 and the corresponding receiver tubes.

A pressure signal is sensed at a static pressure sensing port 45 formed on the interior surface of the passageway 37 in one nozzle housing 35. This static pressure signal is fed through a pressure line 46 to a pressure transducer 47 (see FIG. 1) that provides an output electrical signal that is proportional to the pressure being sensed. The static pressure sensed is a function of the volume of flow past the static pressure sensing port 45 and thus the volume of total inlet flow (40 cfm) can be determined when the pressure at one of the inlets is accurately sensed.

To control the lower volume flow, a venturi indicated at 48 is placed into the line 24, and provides a pressure signal along a line 48A to a pressure transducer 49 that also provides an output electrical signal proportional to pressure in the venturi and which can be used for indicating when the desired flow is passing through line 24. The electrical signals are carried in lines 47A and 49A to a control circuit.

A typical control circuit is shown in FIG. 2. The circuit is essentially the same for controlling both motors, but the circuit shown in FIG. 2 will deal with the control of the butterfly valve 25 in the conduit section 17A for the 38 cubic foot per minute flow. As shown in FIG. 2 the pressure transducer 47 is illustrated, and delivers an output signal along a line 47A. The pressure transducer will be excited in a conventional manner. The transducer can be a solid state pressure sensor, a capacitance pressure sensor or any other desired type of pressure sensor.

A zeroing circuit indicated generally at 50 of a conventional design receives the output from the respective pressure transducer and the units are set so that with no flow in the respective conduits the circuit is balanced at zero. The output is carried along a line 51, which is connected to a summing junction 52. A zero adjust potentiometer 53 can be provided for trimming the zero setting. Any output voltage from the pressure transducer, which may increase as the pressure increases is fed to a summing junction 52. The summing junction 52 also has an input from a reference voltage source 55. The reference voltage source 55 will be set so to have an output voltage that will be equal to the output from the transducer when the desired flow of air in the conduit is achieved with the circuit shown in FIG. 2. A reference voltage adjustment potentiometer indicated at 57 is also provided.

Because the effect of temperature may adversely affect determination of flows at these levels, a temperature sensor, such as a thermistor shown at 60, may be used to provide an output signal along a line 61 to a temperature control circuit 62 that can be adjusted to provide the desired compensation output voltage along the reference voltage output line 63 to the summing junction 52, after taking into account the temperature compensation signal. As the temperature changes the signal along line 61 changes, which adjusts the output reference voltage level on line 63.

The output line 64 from summing junction 52 carries a voltage which represents the error signal, or the difference between the reference voltage on line 63 and the voltage from the transducer which is the pressure dependent, variable voltage on line 51. It is desired to prevent the motors for the flow control valves from "hunting", a dead band circuit 65 is provided. Circuit 65 is of a known circuit which requires an input that has at least a certain level of deviation from an existing setting before an output signal is passed through. A potentiometer 66 can be used for adjusting the input differential needed for exceeding the dead band. In general the dead band circuit used herein is designed so that it will not pass a signal from line 64 until there has been an input signal change equal to approximately one-half of a cubic foot per minute flow variation from a desired level.

Assuming that the error signal 64 is large, as for example when starting up, and is greater than a signal equal to one-half cubic foot per minute flow, an output voltage signal is provided along a line 68 to a time control 69. The time control is a cycling timer that has a switch which is off for a certain number of seconds and then is on for a certain number of seconds so that there is an intermittent drive voltage path to the damper control motor. The time control can be adjusted as to the length of time that is on through an adjustable resistor 70, and the length of time that is off through an adjustable resistor 71. This also is a conventional unit, that provide for intermittent power to the damper motors, so that not only does the output signal from summing junction 52 have to be greater than a selected level different from the desired signal (called the dead band), but it also has to be present at the time when the timer controlled switch is closed, so that the motor will be powered.

The time control is desirably on for half a second at a time, and off for a selected period. The motor 26 drives a one rpm output shaft through a gear set so that the damper movement is very slow. Half a second corresponds to a very small angular movement of the butterfly valve, and thus a very small step of movement of the connected butterfly damper 25 is controlled.

Precise flow control can thus be achieved. Butterfly dampers are essentially non-linear flow volume controls. A half of a degree movement when the damper 25 is almost perpendicular to the axis 27, and thus almost closed, has a significantly greater effect on volume than the same angular movement when the damper 25 is substantially parallel to the axis 27. With the motor 26 off for about six seconds, and then on for a half of a second, for each sampling, very precise adjustment can be achieved without having to have a great deal of hunting.

It also should be noted that a separate signal output line 75 can be provided from the circuit 50, which would carry a signal corresponding to the signal on line 51, and a separate output line 76 can be provided from the temperature compensated output of the reference voltage source 55 to a double pole, double throw switch 77 (labeled S2). The switch 77 has an output line 78 providing a voltage that can be fed to an analog to digital converter and provide a digital output on the face plate of a digital indicator 80, which indicates flow (the signal on line 77) or, if desired, flow setting (the signal on line 76). The error can be obtained by manually subtracting the two readouts.

Thus the simple circuit, and simple mechanical apparatus provides for accurate flow volume control for particle classifiers.

The control to the motor 31 is essentially the same as that shown in FIG. 2, but of course the flows are smaller, so the butterfly could be a smaller size and the conduit can be smaller size as well.

The control of the volume of flow in a classifier provides better cut off size control across a wide range of different operating conditions. The static pressure is sensed for example in an individual nozzle through which a known part of the total flow is passing directly in the interior of the housing for the classifier.

As part of the precise control, the ability to sense the total flow at the interior of a passageway carrying a portion of the total flow using a static pressure sensing line is important. Likewise, mechanical damper control in the conduits carrying the flow insures adequate control of the flow volume.

Although the present invention has been described with reference to preferred embodiments, workers skilled in the art will recognize that changes may be made in form and detail without departing from the spirit and scope of the invention.

What is claimed is:

1. Apparatus for use in combination with an aerosol classifier, having a flow inlet passageway means for carrying inlet flow, and an air pump for providing a flow carrying aerosols through said inlet passageway means, a conduit connecting said air pump and said passageway means to provide the flow, the classifier having means for classifying aerosols and dividing flow into at least two portions, wherein the improvement comprises valve means in said conduit, said valve means being movable and adjustable for adjusting the flow size of the conduit and thus the volume of air passing through the conduit at a substantially constant setting of the air pump, static pressure sensing means in said flow inlet passageway means, a pressure transducer responsive to said static pressure for providing an output signal proportional to the pressure in said flow inlet passageway means, means for comparing said output signal with a reference signal and for providing a drive signal, and a motor for controlling the position of said valve means in said conduit, said motor being operable in response to said drive signal to position the valve means at a position which is related to the drive signal.

2. The apparatus as specified in claim 1 and means for providing the drive signal to the motor only during selected periods of time.

3. The apparatus as specified in claim 1 and means to provide said drive signal to said motor only when the drive signal differs from a reference level by a desired amount.

4. The apparatus as specified in claim 1 wherein said valve means comprises a butterfly valve in said conduit, and said motor has an output shaft that rotates the butterfly valve to change the angle of the plane of the butterfly valve with respect to a longitudinal axis of the conduit.

5. The apparatus as specified in claim 1 wherein said transducer provides an output electrical signal, and the reference signal is an electrical signal, the means for comparing comprising summing junction means for comparing the output electrical signal from the transducer, and the reference signal to provide the drive signal.

6. The apparatus as specified in claim 5 and a temperature compensation circuit for said reference signal, said temperature compensation circuit including a temperature input sensor for sensing ambient temperature and providing a compensation input to the reference signal which is a function of temperature.

7. The apparatus of claim 1 wherein a second conduit is connected between the air pump and the aerosol classifier, the second conduit having a separate flow sensor means therein, and second valve means, a second motor to control the setting of the second valve means, and means responsive to the separate flow sensor means for controlling the volume of flow in the second conduit.

8. The apparatus of claim 7 wherein the second conduit carries substantially less flow than the first mentioned conduit and wherein the air pump has the capacity for providing more than the total inlet flow which flow is limited by the first and second valve means.

9. An aerosol classifier having a through flow and having a flow inlet passageway means for carrying inlet flow, an air pump for providing a flow carrying aerosols through said inlet passageway means into the classifier, a conduit connecting said air pump to said classifier to provide the flow, the classifier having means for classifying aerosols carried by the flow, adjustable opening valve means in said conduit for adjusting the flow volume passing through the flow inlet passageway means and the classifier, static pressure sensing means for sensing static air pressure in said inlet passageway means and for providing an output signal proportional to the static pressure in said inlet passageway means, and means for controlling the valve means in said conduit in response to an output of the static pressure sensing means to adjust the valve means of the static pressure sensing means to adjust the valve means to provide air inlet flow related to the static pressure.

10. The classifier as specified in claim 9 wherein the means for controlling the valve means comprises drive motor means and transducer means for providing a drive signal, means connected to receive the drive signal and for providing it to the motor means only during selected periods of time.

11. The classifier as specified in claim 9 and means for providing said drive signal to said motor means only when the drive signal differs from a reference level by a desired amount.

12. A flow controller for an aerosol classifier having a flow inlet passageway means for carrying inlet flow, an air pump for providing a flow carrying aerosols through said inlet passageway and the classifier, flow carrying means connecting said air pump and said classifier to provide flow through the classifier, adjustable valve means for adjusting the flow through the flow carrying means and thus the volume of air passing through the classifier and the inlet passageway means, static pressure sensing means in said inlet passageway means, a pressure transducer responsive to static pressure sensed at the sensing means for providing an output signal proportional to sensed static pressure in said inlet passageway means, and motor means for controlling the adjustment of said valve means as a function of said output signal to adjust the valve means and the flow through the classifier as a function of the static pressure in the inlet passageway means.

* * * * *